(12) United States Patent
Van Der Louw et al.

(10) Patent No.: US 7,582,622 B2
(45) Date of Patent: Sep. 1, 2009

(54) STEROIDS HAVING A MIXED ANDROGENIC AND PROGESTAGENIC PROFILE

(75) Inventors: Jaap Van Der Louw, Oss (NL); Dirk Leysen, Lokeren (BE); Arij Jan Grootenhuis, Oss (NL); Marcel Evert De Gooijer, Oss (NL)

(73) Assignee: N.V. Organon, Oss (NL)

( * ) Notice: Subject to any disclaimer, the term of this patent is extended or adjusted under 35 U.S.C. 154(b) by 384 days.

(21) Appl. No.: 10/584,006

(22) PCT Filed: Dec. 15, 2004

(86) PCT No.: PCT/EP2004/053475

§ 371 (c)(1),
(2), (4) Date: Jun. 22, 2006

(87) PCT Pub. No.: WO2005/061528

PCT Pub. Date: Jul. 7, 2005

(65) Prior Publication Data

US 2007/0155836 A1 Jul. 5, 2007

(30) Foreign Application Priority Data

Dec. 22, 2003 (EP) .................................. 03104898

(51) Int. Cl.
| | |
|---|---|
| A61K 31/56 | (2006.01) |
| A01N 37/02 | (2006.01) |
| A61K 31/22 | (2006.01) |
| A01N 33/24 | (2006.01) |
| A61K 31/15 | (2006.01) |
| C07C 49/00 | (2006.01) |

(52) U.S. Cl. .................. 514/178; 514/546; 514/640; 568/372

(58) Field of Classification Search ............... 514/178, 514/546, 640; 552/502; 568/372
See application file for complete search history.

(56) References Cited

U.S. PATENT DOCUMENTS

| 3,318,925 | A | | 5/1967 | Anner et al. | ............. 260/397.4 |
|---|---|---|---|---|---|
| 3,318,926 | A | | 5/1967 | Anner et al. | ............. 260/397.4 |
| 3,318,927 | A | | 5/1967 | Anner et al. | ............. 260/397.5 |
| 3,318,928 | A | | 5/1967 | Anner et al. | ............. 260/397.5 |
| 3,318,929 | A | | 5/1967 | Anner et al. | ............. 260/397.5 |
| 3,959,322 | A | | 5/1976 | Hughes et al. | ............. 260/397.4 |
| 4,412,993 | A | * | 11/1983 | Sokolowski | ................. 514/178 |
| 4,788,218 | A | | 11/1988 | Tanabe et al. | ............... 514/510 |

FOREIGN PATENT DOCUMENTS

| FR | 1.434.172 | | 4/1966 |
|---|---|---|---|
| WO | WO 85/05361 | A1 | 12/1985 |
| WO | WO 99/67271 | A1 | 12/1999 |
| WO | WO 00/53619 | A1 | 9/2000 |
| WO | WO 0059920 | A2 | 10/2000 |
| WO | WO 0059920 | A3 | 10/2000 |
| WO | WO 01/05806 | A1 | 1/2001 |

OTHER PUBLICATIONS

Anawalt BD and Amory JK, "Male hormonal contraceptives," Expert Opinion on Pharmacotherapy, Sep. 2001, 2(9), 1389-1398.*
"Androgens" "Goodman & Gilman's The Pharmacological Basis of Therapeutics, 10th ed." Hardman JG, Limbird LE, and Gilman AG EDs., McGraw-Hill, New York, 2001, pp. 1635 and 1643, Snyder PJ, Chapter 59.*
International Search Report for Application No. PCT/EP2004/053475 dated Jul. 5, 2005.
International Preliminary Report for Application No. PCT/EP2004/053475 dated Jun. 26, 2006.
Written Opinion of the International Searching Authority for Application No. PCT/EP2004/053475.
Markiewicz, L. et al., "Estrogenic and Progestagenic Activities of Physiologic and Synthetic Androgens, as Measured by In Vitro Bioassays," Meth. Find. Exp. Clin. Phharmacol., vol. 19, No. 4 (1997) pp. 215-222.
Seaman, W. J., "Canine Ovarian Fibroma Associated with Prolonged Exposure to Mibolerone," Toxicologic Pathology, vol. 13, No. 3 (1985) pp. 177-180.
Ananchenko, S. N. et al., "Syntheses of Derivatives of Oestrane and 19-Norsteroids from 6-Methoxy-Tetralone and 6-Hydroxytetralone," Tetrahedron vol. 18 (1962) pp. 1355-1367.
Avery, M. A. et al., "Synthesis and testing of 17aβ-hydroxy-7 α-methyl-D-homoestra-4, 16-dien-3-one: a highly potent orally active androgen," Steroids, vol. 55 (1990) pp. 59-64.

(Continued)

Primary Examiner—Sreeni Padmanabhan
Assistant Examiner—Paul Zarek
(74) Attorney, Agent, or Firm—Susan Hess

(57) ABSTRACT

The invention provides 19-nor-D-homosteroids, having a mixed androgenic/progestagenic profile, which are orally active, prevent trabecular bone mineral density (BMD) loss, and which lack liver toxicity, having a structure according to the formula (I) wherein, $R^1$ is O, or NOR, with R being hydrogen, (C1-6)alkyl, or (C1-6)acyl, $R^2$ is methyl or ethyl, and $R^3$ is hydrogen or $(C_{1-15})$acyl.

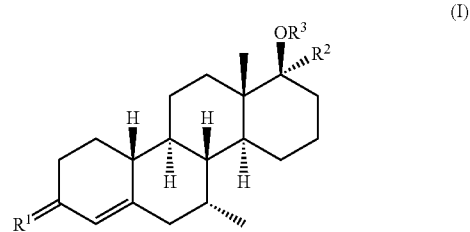

(I)

12 Claims, No Drawings

OTHER PUBLICATIONS

Johns, W. F. et al., "Synthesis and Reactions of 17β-Oxygenated 16α, 17-Cyclopropylandrostanes," J. Org. Chem., vol. 36, No. 14, (1971) pp. 1952.

Ito, Y. et al., "Reaction of 1-Silyloxybicyclo[n.1.0]alkanes with $Fe^{III}Cl_3$. A Facile Synthesis of 2-Cycloalkenones via Ring Enlargement of Cyclic Ketones," J. Org. Chem., vol. 41, No. 11 (1976) pp. 2073-2074.

Schoonen, W.G.E.J. et al., "Notes & Tips," Article No. AB982681, Analytical Biochemistry, vol. 261 (1998) pp. 222-224.

Hakola, K. et al., "Recombinant rat luteinizing hormone; production by Chinese hamster ovary cells, purification and functional characterization," Molecular & Cellular Endocrinology, vol. 128 (1997) pp. 47-56.

van Casteren, J.I.J. et al., "Development of Time-Resolved Immunofluorometric Assays for Rat Follicle-Stimulating Hormone and Luteinizing Hormone and Application on Sera of Cycling Rats," Biology of Reproduction, vol. 62 (2000) pp. 886-894.

\* cited by examiner

STEROIDS HAVING A MIXED ANDROGENIC AND PROGESTAGENIC PROFILE

This application is the National Stage of International Application No. PCT/EP2004/053475, filed Dec. 15, 2004.

The invention relates to compounds having a mixed profile of androgenic and progestagenic activities, to pharmaceutical compositions comprising these compounds and to their use in therapy.

Male contraception seeks to suppress spermatogenesis through the suppression of the gonadotropins luteinizing hormone (LH) and follicle-stimulating hormone (FSH). This results in a depletion of intratesticular testosterone and cessation of spermatogenesis.

Administration of progestagen results in a dose dependent suppression of pituitary gonadotrophins and consequently, a decrease in testosterone levels and a reversible inhibition of spermatogenesis. An exogenous androgen is required to compensate for the reduced testosterone levels.

In the same way, male hormone replacement therapy (HRT) can be accomplished, resulting in replacement of testosterone by an exogenous androgen which is safer on the prostate than endogenous testosterone.

Both, for male contraception and male HRT it would be particularly useful to employ a compound having a mixed profile of androgenic and progestagenic activities. i.e., a compound which possesses both activities intrinsically within one molecule. The aim would be to provide compounds with optimal potency, oral activity, and safety. With regard to safety it is particularly important to minimise the risk of bone loss and liver toxicity.

Compounds with both androgenic and progestagenic properties are known in the art. For example, 7α, 17α-dimethyl-nandrolone (Mibolerone) is a highly active androgen also having progestagenic activity (see e.g. L. Markiewicz et al., Methods and Findings in Experimental and Clinical Pharmacology (1997), 19(4), 215-222). It is orally active but suffers from the drawback of severe liver toxicity (see e.g., J. Seaman, Toxicologic Pathology (1985), 13(3), 177-180).

Certain D-homosteroids are also known to possess a mixed androgenic and progestagenic profile. For instance, (17aβ)-13-ethyl-17a-hydroxy-D-homogon4-en-3-one, (17aβ)-13-ethyl-17a-hydroxy-17a-methyl-D-homogon-4-en-3-one, and (17aβ)13,17a-diethyl-17a-hydroxy-D-homogon-4-en-3-one, which are described in U.S. Pat. No. 3,959,322, are claimed to possess both androgenic and progestagenic activity. We have shown, however, that these compounds are not orally active.

7α-Methyl-19-nor-D-homotestosterone is disclosed as a synthetic intermediate in WO 85/05361. We have shown that this compound possesses a mixed androgenic and progestagenic profile. We have also shown, however, that it is not orally active either.

17aα-Methyl-19-nor-D-homotestosterone, indicated to possess anabolic activity, and in our hands also having progestagenic activity, is described by S.N. Ananchenko et al. in Tetrahedron (1962), 18, 1355-67. We have shown, however, that the compound suffers from a combination of low activity upon oral administration and is unable to prevent trabecular bone mineral density (BMD) loss.

It has now been found, unexpectedly, that within a series of 19-nor-D-homosteroids, mixed androgenic/progestagenic steroids exist which are orally active, which prevent trabecular bone mineral density loss, and which lack liver toxicity. Thus, in a first aspect, the invention provides a series of compounds according to formula I:

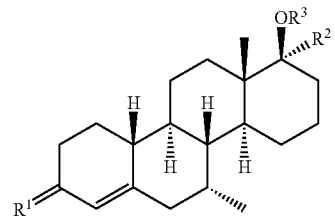

formula I wherein, $R^1$ is O, or NOR, with R being hydrogen, $(C_{1-6})$alkyl or $(C_{1-6})$acyl, $R^2$ is methyl or ethyl, and $R^3$ is hydrogen or $(C_{1-15})$acyl.

In one embodiment, the invention provides compounds according to formula I wherein $R^1$ is O.

In another embodiment, the invention provides compounds according to formula I wherein $R^1$ is O and $R^3$ is hydrogen, i.e., the compounds (7α,17aβ)-17a-hydroxy-7,17a-dimethyl-D-homoestr-4-en-3-one and (7α,17aβ)-17a-ethyl-17a-hydroxy-7-methyl-D-homoestr4-en-3-one, in particular the compound (7α,17aβ)-17a-hydroxy-7,17a-dimethyl-D-homoestr4-en-3-one.

The term $(C_{1-6})$ alkyl represents a branched or unbranched alkyl group having 1-6 carbon atoms. Examples of $(C_{1-6})$ alkyl groups include methyl, ethyl, propyl, isopropyl, butyl, and tertiary butyl.

The term $(C_{1-6})$ acyl and $(C_{1-15})$ acyl represent an acyl group derived from a carboxylic acid having respectively 1-6 and 1-15 carbon atoms. The acyl group can comprise a hydrocarbon which may be branched, unbranched, saturated or unsaturated. Examples of $(C_{1-6})$ acyl groups include formyl, acetyl, propanoyl, propenoyl and pivaloyl, and examples of $(C_{1-15})$ acyl include decanoyl and undecanoyl. Also included within the definition of $(C_{1-6})$ acyl and $(C_{1-15})$ acyl are acyl groups derived from dicarboxylic acids like hemi-maloyl, hemi-succinoyl and hemi-glutaroyl.

The compounds wherein $R^1$ is NOR, with R being hydrogen, $(C_{1-6})$ alkyl or $(C_{1-6})$ acyl, are prodrugs of the compounds wherein $R^1$ is O. Likewise the compounds wherein $R^3$ is $(C_{1-15})$ acyl are prodrugs of the corresponding compounds wherein $R^3$ is hydrogen. Said prodrugs are usually inactive derivatives of the parent compounds which are converted to the active forms in vivo.

The 19-nor-D-homo steroid derivatives of this invention have the natural configurations 8β, 9α, 10β, 13β and 14α. The configuration at C-7 is 7α and at C-17a the configuration is 17aβ.

The compounds of the invention can be synthesised according to methods well known in the art of organic chemistry in general and especially in the art of steroid chemistry. See, for example, Fried, J. and Edwards, J. A., 'Organic Reactions in Steroid Chemistry,' Volumes I and II, van Nostrand Reinhold Company, New York, 1972. A convenient starting material for the preparation of compounds of formula I wherein $R^1$ is O, $R^2$ has the meaning as described above, and $R^3$ is hydrogen is, for example, (7α)-3-methoxy-7-methyl-estra-1,3,5(10)-trien-17-one (i.e. the compound of formula II). This compound can be synthesised using methods well known in the art, see for example, FR 1434172.

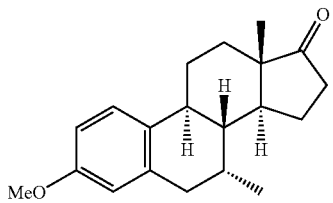
formula II

D-Ring homologation of (7α)-3-methoxy-7-methylestra-1,3,5(10)-trien-17-one can be effected by a number of methods. For example, it can be converted to (7α)-17-(aminomethyl)-3-methoxy-7-methylestra-1,3,5(10)-trien-17-ol followed by treatment with e.g. $NaNO_2/AcOH$ to produce (7α)-3-methoxy-7-methyl-D-homoestra-1,3,5(10)-trien-17a-one (see e.g. Avery, M.A. et al., *Steroids*, 1990, 55, 59). Alternatively, it can be converted to (7α,17β)-3-methoxy-7-methyl-16,17-methylene-17-[(trimethylsilyl)oxy]estra-1,3,5(10)-triene followed by treatment with e.g. iron(III) chloride to produce (7α)-3-methoxy-7-methyl-D-homoestra-1,3,5(10),16-tetraen-17a-one (see e.g. Johns, W.F. et aL, *J. Org. Chem.*, 1971, 36, 1952 and Ito, Y. et al., *J. Org. Chem.*, 1976, 41, 2073). The latter may be converted to (7α)-3-methoxy-7-methyl-D-homoestra-1,3,5(10)-trien-17a-one by e.g. catalytic hydrogenation.

(7α)-3-Methoxy-7-methyl-D-homoestra-1,3,5(10)-trien-17a-one can be treated with methyllithium or ethyllithium, or the corresponding Grignard reagents, optionally in the presence of cerium(III) chloride, to produce a (7α,17aβ)-17a-alkyl-3-methoxy-7-methyl-D-homoestra-1,3,5(10)-trien-17a-ol derivative. The latter may be produced together with the corresponding 17aα-OH,17aβ-alkyl isomer in which case the desired 17aβ-OH,17aα-alkyl isomer is separated from the unwanted latter compound by chromatography or crystallisation. Alternatively, (7α)-3-methoxy-7-methyl-D-homoestra-1,3,5(10)-trien-17a-one can be reacted with, for example, trimethylsulphonium iodide and base to give the 17a-epoxide which can then be converted to the 17aβ-OH, 17aα-methyl compound or 17aβ-OH,17aα-ethyl compound by reaction with a reducing agent (e.g. lithium aluminium hydride or lithium triethylborane) or methylcopper compound (e.g. $Me_2CuLi$), respectively. Birch reduction of the resulting (7α, 17aβ)-17a-alkyl-3-methoxy-7-methyl-D-homoestra-1,3,5,(10)-trien-17a-ol derivative as described in Caine, D. *Org. reactions*, Wiley, New York, 1976, 23, 1, followed by hydrolysis of the $\Delta^{2,5(10)}$ diene derivatives thus obtained then provides (7α,17aβ)-17a hydroxy-7,17a-dimethyl-D-homoestr-4-en-3-one or (7α,17aβ)-17a-ethyl-17a-hydroxy-7-methyl-D-homoestr-4-en-3-one.

Compounds of the invention wherein $R^1$ is NOR with R being hydrogen, $(C_{1-6})$alkyl or $(C_{1-6})$acyl and compounds of the invention wherein $R^3$ is $(C_{1-15})$acyl are readily obtained by methods well known in the art. For example, compounds of the invention wherein $R^3$ is $(C_{1-15})$ acyl are readily obtained by acylation of the corresponding precursors wherein $R^3$ is hydrogen using, for example, an acylation agent such as the desired acid chloride in the presence of a base such as triethylamine.

The 19-nor-D-homosteroids of the invention are suitable for use in therapy, e.g., inter alia in male contraception and male HRT. With male HRT is meant androgen supplementation as well as testosterone replacement.

Administration of a compound according to the invention will be greatly aided by the manufacture of pharmaceutical compositions. The present invention therefore also relates to a pharmaceutical composition comprising a compound according to the invention mixed with a pharmaceutically acceptable excipient, such as the ones described in Gennaro et al., Remmington: *The Science and Practice of Pharmacy*, $20^{th}$ Edition, Lippincott, Williams and Wilkins, 2000; see especially part 5: pharmaceutical manufacturing. Suitable excipients are made available e.g., in the Handbook of Pharmaceutical Excipients, $2^{nd}$Edition; Editors A. Wade and P. J. Weller, American Pharmaceutical Association, Washington, The Pharmaceutical Press, London, 1994. The mixtures of a compound according to the present invention and a pharmaceutically acceptable excipient may be compressed into solid dosage units, such as tablets, or be processed into capsules or suppositories. For making dosage units e.g., tablets, the use of conventional additives such as fillers, colorants and polymeric binders is contemplated. In general, any pharmaceutically acceptable additive, which does not interfere with the function of the active compounds can be used. Suitable fillers with which the pharmaceutical compositions can be prepared and administered include lactose, starch, cellulose and derivatives thereof, or mixtures thereof used in suitable amounts.

Male contraception frequently is described to comprise a regimen of administration of hormones in which a progestagen serves to achieve a contraceptive effect and an androgen serves to supplement the resulting decreased testosterone level. The combined androgenic/progestagenic nature of the compounds of the invention allows the achievement of male contraception through the progestagen-androgen system on the basis of one single compound.

Thus, the invention also relates to the use of a steroid compound according to the invention for the manufacture of a medicament having contraceptive activity (for which in the art the term 'contraceptive agent' is also used).

The invention pertains to a method of contraception, comprising administering to a fertile male, notably human, a compound according to the invention in a dosage amount and regimen, which is sufficient for said compound to be contraceptively effective per se, and which simultaneously serves to maintain a sufficient androgen level in the male subject to this contraceptive method. Alternatively, the method of contraception provided by the present invention comprises administering to a fertile male, notably human, a contraceptively effective combination of a sterilitant, such as a progestagen, and a compound according to the invention. As a second alternative, the method of contraception involves the administration of a compound according to the invention as the (progestagenic) sterilitant, wherein the maintenance of a sufficient androgen level is taken care of, in part, by the androgenic activity of the compound of the invention, and which is supplemented by an additional androgen.

The invention also pertains to a kit for male contraception comprising means for the administration of a progestagen and means for the administration of an androgen, characterised in that one of the means is a pharmaceutical composition comprising a compound according to the present invention.

The androgenic/progestagenic compounds of the invention can also be used for testosterone supplementation in the partially androgen deficient (ageing) male.

The androgenic/progestagenic compounds of the invention can also be used for (partial) replacement of endogenous testosterone. The progestagenic activity leads to an advantage of the compounds of the invention in that the production of endogenous testosterone is suppressed. The androgenic activity serves to compensate for the resulting testosterone deficiency. This allows replacement of testosterone by an exogenous androgen, which is safer than endogenous testosterone. Endogenous testosterone is converted by 5α-reductase to the more potent 5α-dihydrotestosterone resulting in well known detrimental effects such as prostate problems, acne and hair loss. Hence by virtue of the androgenic/progestagenic compounds of the invention, one can advantageously diminish the intrinsic detrimental effects of endogenous testosterone . Therefore, and more specifically, the compounds of the invention can be used for the treatment of benign prostate hypertrophy (BPH).

Optionally, the androgenic/progestagenic compounds of the invention can be combined with an androgen known in the art which is not 5α-reducable, such as MENT, or the androgens disclosed in WO 99/67271, WO 00/53619, WO 00/59920 or WO 01105806, or a progestagen known in the art.

Thus, the invention also relates to the use of a compound according to the invention for the manufacture of a medicament for the treatment of androgen insufficienc y or a medicament for testosterone replacement. The person skilled in the art will appreciate that this use can comprise the combined administration of a compound according to the invention and an androgen or alternatively the combined use of a compound according to the invention and a progestagen. Accordingly, the invention also includes a method of treatment in the field of male hormone replacement therapy comprising the administration, to a male of a compound as described hereinbefore (in a suitable pharmaceutical dosage form).

The invention also pertains to a method of treatment comprising administering to a male in need of androgen supplementation or testosterone replacement a therapeutically effective amount of a compound according to the invention, optionally in combination with an androgen known in the art, or a progestagen known in the art.

The invention is illustrated with the following examples.

EXAMPLE 1

Preparation of (7α,17aβ)-17a-hydroxy-7,17a-dimethyl-D-homoestr4-en-3-one (7α, 17aβ)17a-Hydroxy-7,17a-dimethyl-D-homoestr4-en-3-one i)—A solution of diisopropylamine (42.4 ml) in dry tetrahydrofuran (294 ml) was cooled to −30° C. n-BuLi (1.6 M solution in hexanes, 173 ml) was added dropwise (T <−10° C.) and stirring was continued at −30° C. for 10 min. The reaction mixture was cooled to −78° C. and a solution of (7α)-3-methoxy-7-methylestra-1,3,5(10)-trien-17-one [see FR 1434172; 25.0 g] in dry tetrahydrofuran (398 ml) was added dropwise. Stirring was continued for 1 h at −78° C. Chlorotrimethylsilane (31.5 ml, freshly destilled from CaH) was added and the temperature was allowed to rise to room temperature. The mixture was stirred for 30 min. after addition of TMSCl, cooled to 0° C., and then quenched with a saturated aqueous solution of ammonium chloride. The mixture was extracted with ethyl acetate; the combined organic phases were washed with brine, dried over sodium sulfate and concentrated under reduced pressure, to give (7aα)-3-methoxy-7-methyl-17-[(trimethylsilyl)oxy]estra-1,3,5(10),16-tetraene (35.5 g). The product was used in the following step without further purification.

ii)—A solution of the product obtained in the previous step (35.5 g) and diiodomethane (27.3 ml) in dry dichloromethane (503 ml) was cooled to 0 C. A solution of diethylzinc in hexane (15% wt., 305 ml) was added (T<5° C.), the ice-bath was removed and the reaction mixture was stirred for 1 h at room temperature. Ice was added, the reaction mixture was poured into a saturated aqueous solution of ammonium chloride and the mixture was extracted with ethyl acetate. The combined organic phases were washed with brine, dried over sodium sulfate, and concentrated under reduced pressure, to give (7aα)-3-methoxy-7-methyl-16,17-methylene-17-[(trimethylsilyl)oxy]estra-1,3,5(10)-triene (35.5 g). The product was used in the following step without further purification.

iii)—A solution of the product obtained in the previous step (35.5 g) in dry dimethylformamide (169 ml) was added to an ice-cooled solution of iron(III) chloride (very dry, 40.8 g) in the same solvent (169 ml). The ice bath was removed and the reaction mixture was stirred for 1.5 h at room temperature. Under cooling, the mixture was quenched dropwise with aqueous hydrochloric acid (2 M). The mixture was poured into water and extracted with ethyl acetate; the combined organic phases were washed with water and brine, dried over sodium sulfate and concentrated under reduced pressure. Column chromatography afforded (7α)-3-methoxy-7-methyl-D-homoestra-1,3,5(10),16-tetraen-17a-one (10.0 g).

iv)—A suspension of palladium on activated carbon (10%; 5 g) in water (50 ml) was added to a solution of the product obtained in the previous step (67 g) in a mixture of ethanol (1250 ml) and THF (250 ml) and the mixture was stirred under hydrogen (5 bar) at room temperature overnight. A sample of the reaction mixture was filtered over celite and the filtrate was concentrated under reduced pressure. $^1$H-NMR indicated a conversion of 70%. Another portion of Pd/C (10%, 2.5 g) was added and stirring under hydrogen (5 bar) was continued overnight. Work-up as described above afforded (7α)-3-methoxy-7-methyl-D-homoestra-1,3,5(10)-trien-17a-one (61 g). The product was used in the following step without further purification.

v)—A mixture of methyl lithium (1.4 M solution in diethyl ether, 475 ml) and dry THF (5000 ml) was cooled to −40° C. A solution of the product obtained in the previous step (54 g) in dry THF (1000 ml) was added and the reaction mixture was stirred at room temperature overnight. The mixture was poured into a saturated aqueous solution of ammonium chloride (7500 ml) and extracted with ethyl acetate. The combined organic phases were washed with brine, dried over sodium sulfate and concentrated under reduced pressure. Column chromatography afforded (7α,17aβ)-3-methoxy-7,17a-dimethyl-D-homoestra-1,3,5(10)-trien-17a-ol (19.9 g).

vi)—The product obtained in the previous step (1.0 g) in dry tetrahydrofuran (25 ml) was added to liquid ammonia (100 ml), cooled to −45° C. Lithium (0.65 g) was added and the reaction mixture was stirred at −45° C. for 2 h. A mixture of 2-propanol (10 ml) and dry THF (10 ml) was added dropwise and the mixture was stirred overnight while allowing the ammonia to evaporate. A saturated aqueous solution of ammonium chloride (100 ml) was added followed by ethyl acetate (250 ml). The mixture was extracted with ethyl acetate. The combined organic phases were washed with brine, dried over sodium sulfate and concentrated under reduced pressure, to give (7α,17aβ)-3-methoxy-7,17a-dimethyl-D-homoestra-2,5(10)-diene-17a-ol (1.02 g). The product was used in the following step without further purification.

vii)—A solution of the product obtained in the previous step (1.02 g) in acetone (50 ml) was treated with hydrochloric acid (6 M, 5 ml). After 2 h stirring at room temperature, the reaction mixture was neutralized with a saturated aqueous solution of sodium hydrogencarbonate and the product was extracted into ethyl acetate. The combined organic phases were washed with brine, dried over sodium sulfate and concentrated under reduced pressure. Crystallization afforded (7α,17αβ)17a-hydroxy-7,17a-dimethyl-D-homoestr-4-en-3-one (m.p. 152° C.).

EXAMPLE 2

Preparation of (7α,17aβ)-17aethyl-17a-hydroxy-7-methyl-D-homoestr-4en-3-one (7α,17aβ)-17a-Ethyl-17a-hydroxy-7-methyl-D-homoestr4-en-3-one i)—A suspension of cerium(III) chloride (1.8 g) in dry tetrahydrofuran (40 ml) was stirred overnight and then cooled to −78° C. Ethylmagnesium chloride in tetrahydrofuran (25%, 3.3 ml) was added and stirring was continued for 1 h. Solid (7α)-3-methoxy-7-methyl-D-homoestra-1,3,5(10)-trien-17a-one [Example 1, step iv; 0.50 g] was added and the reaction mixture was allowed to reach room temperature in 1.5 h. The mixture was poured into a saturated aqueous solution of ammonium chloride and the product was extracted into ethyl acetate. The combined organic phases were washed with brine, dried over sodium sulfate and concentrated under reduced pressure. Column chromatography afforded (7α,17aβ)-17a-ethyl-3-methoxy-7-methyl-D-homoestra-1,3,5(10)-trien-17a-ol (0.11 g).

ii)—The product obtained in the previous step (0.11 g) in dry tetrahydrofuran (10 ml) was added to refluxing liquid ammonia (50 ml). Lithium (0.65 g) was added and the reaction mixture was stirred for 10 min. A solution of tert-butanol in tetrahydrofuran was added and stirring was continued for another 1.5 h. After cooling to −78° C., the mixture was quenched with ethanol and the ammonia was allowed to evaporate. Water was added and the product was extracted into ethyl acetate. The combined organic phases were washed with brine, dried over sodium sulfate and concentrated under reduced pressure, to give (7α,17aβ)-17a-ethyl-3-methoxy-7-methyl-D-homoestra-2,5(10)-dien-17a-ol. The product was used in the following step without further purification.

iii)—Following a procedure analogous to that described under vii of Example 1, the product obtained in the previous step was converted to (7α,17aβ)-17a-ethyl-17a-hydroxy-7-methyl-D-homoestr4-en-3-one (0.071 g). $^1$H-NMR (CDCl$_3$) 5.83 (bs, 1H), 2.48-0.94 (m), 0.90 (t, 3H, J=7.8 Hz), 0.72 (d, 3H, J=7.4).

EXAMPLE 3

Androgenic and Progestagenic Agonistic Activity of the Compounds of the Invention The compounds according to the invention were tested for androgenic activity and for progestagenic activity.

The transactivative androgen agonistic activity of the compounds of the invention was measured in Chinese hamster ovary cells (CHO) transfected with the human androgen receptor (hAR), in combination with a mouse mammary tumor virus (MMTV), and luciferase receptor gene (incubation time 16 h, temperature 37° C.) and compared with the activity of 5α-dihydrotestosterone [according to the procedure described by Schoonen, W. G. E. J. et aL., Analyt. Biochem. 261, 222-224 (1998)].

The transactivative progestagenic agonistic activity of the compounds of the invention was measured in Chinese hamster ovary cells (CHO) transfected with the human progesterone receptor B (hPRB), in combination with a mouse mammary tumor virus (MMTV), and luciferase receptor gene (incubation time 16 h, temperature 37° C.) and compared with the activity of (16α)-16-ethyl-21-hydroxy-19-norpregn-4ene-3,20-dione [according to the procedure described by Schoonen, W. G. E. J. et al., Analyt. Biochem. 261, 222-224 (1998)]. Results are collected in Table 1.

The LH Suppression Assay

The in vivo potency of the compounds of the invention was determined in a mature male castrated rat model.

In this model serum LH is high (about 20× fold higher than with intact rats, due to the absence of the negative feedback of testicular testosterone). These rats are p.o. treated for 4 days daily with a given compound of the invention in a suspension fluid of arachis oil or arachis oil +5 or 10% ethanol. Before dosing and 3 hours after the last oral dose blood is collected via tail vein and in the serum LH is determined. Potency (p.o.) of the compounds of the invention (minimal active dose, MAD) is expressed as the amount (mg/kg) of a compound of the invention which suppresses serum LH for 65% (with a 95% confidence interval).

The rat LH Time-Resolved Immuno Fluorometric Assay (TR-IFMA) has been developed in house using home made reagents, a monoclonal catching antibody directed against the β-subunit of human chorion gonadotrophin (hCG, which cross reacts with rat β-subunit) and a biotin labelled detecting antibody (rabbit polydonal antibody directed against the alfa-subunit of recombinant rat LH). Recombinant rat LH was prepared according to known methods, e.g., the method described by Hakola et aL., Molecular & Cellular Endocrinology (1997), 128, 47-56. In this two-site-IFMA, only intact rat LH is determined by a final incubation with streptavidin-europium. The detection in the IFMA is based on fluorescence of the lanthanide europium during a relative long excitation period. The concentration range of rat LH standard is 0.001-10 ng/ml, for optimal accuracy measurements of serum LH serum samples were diluted 8-times with assay buffer (J. I. van Casteren et al., Biol. Reprod. (2000), 62, 886-894). Results are collected in Table 1.

TABLE 1

Androgenic and progestagenic agonistic activity/LH suppression data of compounds of the invention (Examples 1 and 2) and prior art compounds (A-C).

| Compound | Androgenic Activity (%) | Progestational Activity (%) | LH-Suppression MAD po (mg/kg) |
|---|---|---|---|
| Cpd of Example 1 | 42.9 | 53.3 | 8.5 |
| Cpd of Example 2 | 9.9 | 29.7 | 10 |
| Reference compound A | 71.6 | 98.0 | >30 |
| Reference compound B | 25.3 | 10.6 | >30 |
| Reference compound C | 220 | 45 | 1.0 |

Reference compound A: (17aβ)-17a-Hydroxy-17a-methyl-D-homoestr-4-en-3-one.
Reference compound B: (7α,17aβ)-17a-Hydroxy-7-methyl-D-homoestr-4-en-3-one.
Reference compound C: (7α,17β)-17-Hydroxy-7,17-dimethylestr-4-en-3-one (Mibolerone).

Anti-Osteoporosis Test in Mature Male Castrated Rats (6 Weeks Treatment)

In this test the oral efficacy of a compound of the invention for the prevention of castration-induced trabecular bone mineral density (BMD) loss in male rats was evaluated.

Mature male Wistar rats (350-400 g) were used. Orchidectomy (orx) or sham operation was performed under isoflurane anaesthesia. After recovery of anaesthesia, within 24 hours, rats were treated once daily for 6 weeks p.o. with different doses of the compounds of the invention or vehicle only (placebo intact, placebo orx) with a volume of 1 ml/kg (n=5). One day after the last administration autopsy is performed and the right femur is dissected out. Trabecular bone mineral density of the metaphysal part of the femur was measured with a pQCT (peripheral Quantitative Computed Tomography machine; XCT 960A, Stratec, Birkenfeld, Germany). Results are collected in Table 2.

TABLE 2

Results from osteoporosis assay.

| Compound | Dose | BMD (gmean ± sem) | Mean proportional difference in bone density |
| --- | --- | --- | --- |
| Placebo intact | 0 mg/kg | 217 ± 27 | 100% |
| Placebo orx | 0 mg/kg | 100 ± 17 | 0% |
| Cpd of Example 1 | 8 mg/kg | 255 ± 22 | 133% |
| Reference compound A | 16 mg/kg | 133 ± 20 | 28% |

Determination of Liver Safety: the BSP Retention Assay

The primary aim of this test was the evaluation of liver function, by measuring the clearance of a single, i.v. injected, dose of bromosulfophthalein (BSP) after 7 days (once daily) p.o. treatment of male castrated rabbits.

Briefly, this test was performed in mature male castrated NZW rabbits. At least two weeks after castration animals were treated for seven days (once daily) with compounds of the invention in tablets or in vehicle arachis oil +5% ethanol resulting in doses of 10 mg/kg. Twenty-four hours after the last administration the rabbits were lightly sedated with 0.15 ml Hypnorm i.m., and BSP was injected (15 mg/kg i.v., dissolved in 5% (w/v) mannitol/$H_2O$). Blood was collected at 5, 10, 15 and 20 minutes, and BSP content in plasma was determined with a spectrophotometer. The T½ with respect to BSP was calculated from the obtained data (see Table 3).

TABLE 3

BSP data of a compound of the invention.

| Compound | Vehicle | T½ BSP (min.) |
| --- | --- | --- |
| Cpd of Example 1 | Tablet | 6.3 |
| Testosterone | Tablet | 5.2 |
| Reference compound C | Tablet | 13.6 |
| Cpd of Example 1 | Arachis oil + 5% ethanol | 4.6 |
| Testosterone | Arachis oil + 5% ethanol | 4.2 |
| Reference compound C | Arachis oil + 5% ethanol | 7.1 |

What is claimed is:

1. A compound of formula I,

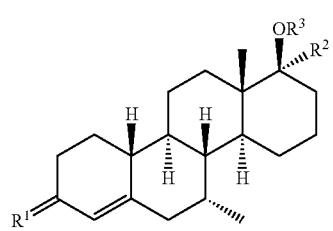

formula I wherein,
$R^1$ is O, or NOR, with R being hydrogen, $(C_{1-6})$ alkyl or $(C_{1-6})$ acyl,
$R^2$ is methyl or ethyl, and
$R^3$ is hydrogen or $(C_{1-15})$ acyl.

2. A compound according to claim 1, wherein $R^1$ is O.

3. A compound according to claim 1, wherein $R^1$ O and $R^3$ is hydrogen.

4. The compound (7α,17aβ)-17a-hydroxy-7,17a-dimethyl-D-homoestr-4-en-3-one.

5. A pharmaceutical composition comprising a compound according to claim 1 and a pharmaceutically acceptable excipient.

6. The compound according to claim 2, wherein $R^1$ is O and $R^3$ is hydrogen.

7. A pharmaceutical composition comprising a compound according to claim 2 and a pharmaceutically acceptable excipient.

8. A pharmaceutical composition comprising a compound according to claim 3 and a pharmaceutically acceptable excipient.

9. A pharmaceutical composition comprising a compound according to claim 4 and a pharmaceutically acceptable excipient.

10. A pharmaceutical composition comprising a compound according to claim 6 and a pharmaceutically acceptable excipient.

11. A method of contraception, comprising administering to a male patient an effective amount of a compound according to claim 1.

12. A method of treating androgen insufficiency, comprising administering to a male patient suffering from androgen insufficiency an effective amount of a compound according to claim 1.

* * * * *

UNITED STATES PATENT AND TRADEMARK OFFICE
CERTIFICATE OF CORRECTION

PATENT NO. : 7,582,622 B2
APPLICATION NO. : 10/584006
DATED : September 1, 2009
INVENTOR(S) : Van Der Louw et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this

Fourteenth Day of September, 2010

David J. Kappos
*Director of the United States Patent and Trademark Office*